(12) United States Patent
Andreussi

(10) Patent No.: US 10,473,563 B2
(45) Date of Patent: Nov. 12, 2019

(54) METHOD AND APPARATUS FOR THE ISOKINETIC SAMPLING OF A MULTIPHASE STREAM

(71) Applicant: TEA SISTEMI S.P.A., Pisa (IT)

(72) Inventor: Paolo Andreussi, Pisa (IT)

(73) Assignee: TEA SISTEMI S.P.A., Pisa (IT)

( * ) Notice: Subject to any disclaimer, the term of this patent is extended or adjusted under 35 U.S.C. 154(b) by 81 days.

(21) Appl. No.: 15/525,101

(22) PCT Filed: Nov. 9, 2015

(86) PCT No.: PCT/IB2015/058641
§ 371 (c)(1),
(2) Date: May 8, 2017

(87) PCT Pub. No.: WO2016/075610
PCT Pub. Date: May 19, 2016

(65) Prior Publication Data
US 2017/0315026 A1    Nov. 2, 2017

(30) Foreign Application Priority Data

Nov. 10, 2014 (IT) .................. 102014902307985

(51) Int. Cl.
*G01N 1/20* (2006.01)
*G01N 1/22* (2006.01)
(Continued)

(52) U.S. Cl.
CPC .......... *G01N 1/2035* (2013.01); *G01F 1/36* (2013.01); *G01F 1/40* (2013.01); *G01F 1/74* (2013.01);
(Continued)

(58) Field of Classification Search
CPC .......... G01N 1/2247; G01N 2001/105; G01N 2001/1062; G01N 2001/225; G01N 1/2035; G01F 1/36; G01F 1/37; G01F 1/40; G01F 1/74; G01F 1/42; G01F 1/44; G01F 1/46
See application file for complete search history.

(56) References Cited

U.S. PATENT DOCUMENTS

| 4,942,774 A | 7/1990 | McFarland |
| 5,337,595 A | 8/1994 | Lewis |

(Continued)

FOREIGN PATENT DOCUMENTS

| EP | 1163495 B1 | 8/2003 |
| WO | 2005031311 A1 | 4/2005 |

(Continued)

OTHER PUBLICATIONS

International Search Report and Written Opinion for International Application No. PCT/IB2015/058641 ( dated Mar. 18, 2016) (11 pages).

*Primary Examiner* — Justin N Olamit
(74) *Attorney, Agent, or Firm* — Lucas & Mercanti, LLP

(57) ABSTRACT

The present invention refers to a method for the isokinetic sampling of liquids and gases present in streams having many fluid phases, and to an apparatus suitable for achieving it. The method and apparatus have application in particular in the field of oil extraction, wherein, after the extraction of liquid and gaseous hydrocarbons possibly accompanied by water and suspended solids, it is necessary to know the composition of the mixture extracted and also the flow rate of the single phases.

10 Claims, 3 Drawing Sheets

(51) Int. Cl.
*G01F 15/08* (2006.01)
*G01F 1/40* (2006.01)
*G01F 1/74* (2006.01)
*G01F 1/36* (2006.01)

(52) U.S. Cl.
CPC .............. *G01F 15/08* (2013.01); *G01N 1/20* (2013.01); *G01N 1/22* (2013.01); *G01N 1/2247* (2013.01); *G01N 2001/225* (2013.01); *G01N 2001/2267* (2013.01); *G01N 2001/2285* (2013.01)

(56) References Cited

U.S. PATENT DOCUMENTS

| | | | |
|---|---|---|---|
| 6,546,809 B1 * | 4/2003 | Andreussi | E21B 43/34 73/861.04 |
| 6,553,848 B1 | 4/2003 | Tallentire et al. | |
| 7,131,451 B2 * | 11/2006 | Nugent | G01F 1/42 137/12 |
| 7,650,799 B2 * | 1/2010 | Atkinson | G01F 1/44 73/861.52 |
| 7,942,065 B2 * | 5/2011 | Xie | G01F 15/02 73/861.04 |
| 2012/0234103 A1 | 9/2012 | Boschi et al. | |

FOREIGN PATENT DOCUMENTS

WO   2007060386 A1   5/2007
WO   2011039593 A1   4/2011

\* cited by examiner

METHOD AND APPARATUS FOR THE ISOKINETIC SAMPLING OF A MULTIPHASE STREAM

CROSS-REFERENCE TO RELATED APPLICATIONS

This application is a 371 of PCT/IB2015/058641, filed Nov. 9, 2015, which claims the benefit of Italian Patent Application No. 102014902307985, filed Nov. 10, 2014.

FIELD OF THE INVENTION

The present invention refers to a method for the isokinetic sampling of different fluids present in multi-phase streams, i.e. consisting of many fluid, liquid and gaseous phases, possibly also in the presence of solids. The present method and the relative apparatus have application in particular in the field of oil extraction, wherein, after the extraction of liquid and gaseous hydrocarbons possibly accompanied by water and suspended solids, it is necessary to know the composition of the extracted mixture, as well as the flow-rate of the single phases. The present method and the relative apparatus also have application in industrial plants that foresee to send to chemical reactors, or to purification plants, process fluids consisting of many phases, for which it is necessary to continuously monitor the composition.

STATE OF THE ART

In industry the sampling of streams consisting of many fluid phases foresees to extract a sample of fluid that is significant in terms of composition and of volumetric fractions of the present phases from the pipes that transport these streams, even in high temperature and pressure conditions. Such sampling can be carried out with a method that is known as "isokinetic sampling". With reference to FIG. 1$a$ attached hereto a piece of vertical pipe with constant section of the known type is shown, in which the isokinetic sampling is carried out using one or more sampling probes consisting of tubes having a small diameter and extracting a flow rate in volume of sampled fluid that is equal to the section of the sampling probe(s), multiplied by the local velocity of the fluid and solid phases at the sampling probe(s). The sampling carried out in this way does not cause disturbances to the main stream, disturbances that could alter the composition of the overall fraction of the stream that is sampled. This operation is particularly easy in the case of flows characterised by good mixing in the flow section of the pipeline thanks to conditions of turbulent motion, i.e. the presence of a known system of mixing the fluids, like for example narrowed sections, mixers or other.

In order to obtain isokinetic sampling the sampled flow rate is regulated by acting on the pressure of the separator or container to which the sampled fluid is sent downstream of the sampling probe, based on the values of the pressure difference between a section of the main pipeline located immediately upstream of the sampling probe and a section located immediately downstream, according to the scheme shown in FIG. 1$a$, forcing this difference to be equal to zero based on a law of physics known as Bernoulli's Law. In particular, this method is normally used for the isokinetic sampling of a stream consisting of a single fluid phase.

In the case of streams consisting of many fluid phases, also possibly in the presence of solids, the simple method described above and illustrated in FIG. 1$a$ may not be effective for various reasons, starting from the non-homogeneity of the composition of the multiphase stream. A second possible error source consists of the measurement of the pressure difference between the sections immediately upstream and downstream of the sampling section, in particular in the presence of many fluid phases that move at low speed, since the pressure differences to be measured can be very small or have substantial variations in time due to the presence of slugs of liquid alternating with gas bubbles.

In the case of flows with slugs, the sampling may, in the case for example of sampling from a pipe for production or transportation of liquid and gaseous hydrocarbons, consist of a fraction of the liquid phase that is less than the average value present in the pipeline and a larger fraction of the gaseous phase. This circumstance can occur since, at the moment at which the sampling probe comes across a slug of liquid, the sampling is less than expected due to the greater density of the liquid with respect to the gas. The opposite occurs with the gas, in this way altering the liquid-gas ratio in the sampled mixture.

The available data collected up to now shows how this possible measurement error source can be significant in flow conditions with slugs, whereas it is absent in flow conditions in which the fluid phases are well mixed, like for example a flow of gas accompanied by a small fraction of liquid. The aforementioned sampling error can be substantially reduced by causing a strong mixing of the fluid phases present in the pipe. The mixing, however, requires the use of known methods and apparatuses, such as flow restrictions, static mixers, etc., which cause an often unwanted increase in pressure losses in the pipe.

For example, devices like those described in international patent applications WO 2005/031311 and WO 2007/060386, which use single-inlet sampling probes, have the limitation of operating correctly only in the presence of a continuous gaseous phase containing dispersed droplets, or a continuous liquid phase containing dispersed gas bubbles, whereas they are less effective in the case of high fractions of liquid in flow conditions with slugs. Moreover, these isokinetic sampling devices allow the flow-rates of liquid and of gas of the multiphase mixture to be characterised only coupled with the measurement of the total flow rate of the multiphase stream that is independent from the sampling.

These possible drawbacks are only in part present in the method and in the relative apparatus for the measurement of a multiphase flow presented in European patent No. EP1163495, in which the same inventor of the present invention proposes the scheme illustrated in FIG. 1$b$. The measurement apparatus according to such a patent foresees a flow section of the measurer in which conditions of mixing between the phases present are made ($U_L$, $U_G$ uniform in the section, even if in general variable over time). In this section a part $q_C$ of the total flow of flow rate Q is sampled, with the sum of the sampled flow and of the non-sampled flow being equal to the total flow entering the measurer Q. Using A to indicate the flow area at the sampling section and $A_C$ to indicate the area of the sampling section, isokinetic sampling conditions are obtained if the sampled flow rate is equal to the fraction $A_C/A$ of the total flow rate of the fluid through the section A.

In the case of isokinetic sampling of the phases, where $q_L$ and $q_G$ define the flow-rates of the liquid and gaseous phase measured after the separation of the sampled phases, and $Q_L$ and $Q_G$ define the total flow-rates of liquid and of gas entering the measurer, the following relationships are valid:

$$Q_L = q_L A/A_C, \quad (1)$$

$$Q_G = q_G A/A_C, \quad (2)$$

Therefore, in the case of isokinetic sampling of the phases, according to this patent, the total flow-rates of liquid and of gas $Q_L$ and $Q_G$ can be obtained directly from the flow-rates $q_L$ and $q_G$ measured after the sampling and the separation.

In such a patent, it is foreseen to carry out an isokinetic sampling of the phases using a method that uses one or two calibrated flanges, shown in FIG. 1b, crossed by the multiphase mixture, operating according to two possible procedures: i) discontinuously, using the calibrated flange located downstream of the sampling as reference for the measurement. This flange is crossed at different times or exclusively by the fraction of flow that is not sampled, i.e. by closing a suitable valve, from the totality of the flow fed to the measurer. Alternatively, ii) continuously, using a calibrated flange arranged upstream and a second flange arranged downstream of the sampling section as reference for the measurement.

The discontinuous method foresees to carry out the measurements at subsequent times. Therefore, this procedure does not ensure that measurements carried out at different times refer to equal flow-rates of the phases entering the measurer in the case of flows that are variable over time. In the continuous method, the flange arranged upstream of the sampling section and of the second flange causes a significant mixing of the fluid phases present. After mixing, the characteristics of the multiphase mixture that flows through the first and second flange are different and consequently the pressure drops through the two calibrated flanges that are used to ensure the isokinetic nature of the sampling can provide results dependent on the amount of mixing and the flow conditions, as well as on the value of the liquid and gas flow-rates.

The apparatus as described in EP1163495 has the limitation of being subject to errors in the measurement of the load losses $\Delta p$ that the flow undergoes in at least one flow restriction following fluctuations over time of the flow-rates in the case of discontinuous measurement, and the variations of the fluid-dynamic characteristics of the multiphase mixture in the case of continuous measurement. Added to this is the fact that the discontinuous measurement requires the intervention of an expert operator not only to act on the valve, but also for the analysis of the measurements thus obtained and for the adjustment of the valve that controls the sampling.

A different device based on an analogous principle and again described by the same inventor in international patent application No. WO 2011/039593 foresees that the overall flow that reaches the sampling section is divided into a large number n of identical channels, exemplified in the patent as being 20 in number, among which m are sampling channels, for example 2 out of 20 in the case in which 10% of the mixture is intended to be sampled. The sampling is isokinetic if, also in this case like for the case illustrated in FIG. 1a applying Bernoulli's law, the pressure difference between the sampling channels and the non-sampling channels immediately downstream of the inlet of the channels is zero. For this purpose, it is possible to act on a valve for regulating the sampling flow rate.

The configuration described in WO 2011/039593 makes it possible to have an effective sampling of the phases present, but it causes pressure losses that are still significant in the sampling section due to the configuration of such a section (widening of the flow section and subsequent narrowing, splitting and joining back together of the flow-rates of the single channels, etc.). These pressure losses are added to with the pressure losses caused by the mixing section of the phases that is necessary before the sampling section. Finally, in addition there are the losses caused by the calibrated flange that follows the sampling section and is used for the continuous control of the process. In conclusion, this method, despite being potentially effective in terms of accuracy of measurement, requires an overall pressure loss that can be excessive. A second limit of this method consists of the bulk and the significant cost of the sampling section, a section that foresees a large number of ducts in parallel and has a greater constructive complexity with respect to the method described hereinafter.

For the aforementioned reasons, the technical problem of having a method and relative apparatus for the isokinetic sampling of multiphase fluid streams, which also allows a correct measurement of the flow rate of the different single phases present in such streams to be carried out, without having the limitations and the drawbacks illustrated above for the known methods, remains unsolved.

SUMMARY OF THE INVENTION

The purpose of the present invention is to provide an apparatus and a method for the isokinetic sampling of a fluid multiphase stream characterised by low load losses and able to be used even in the case of flow conditions that are variable in time and space.

The apparatus and the method of the invention are based on an isokinetic sampling hereinafter also called Dual Orifice Sampling, and foresee the use of two distinct concentric flow restrictions arranged parallel to each other according to different geometries as described in detail hereinafter, respectively crossed by the sampled and non-sampled fluid. The flow restrictions are located in the same flow section and therefore at the moment of sampling the two fluid streams have undergone the same level of mixing.

A further purpose of the invention is to provide a sampling apparatus and method that ensure isokinetic sampling conditions of the multiphase stream, and a method for the measurement of the flow rate of the single liquid and gaseous phases present in said stream in which the sampling of the stream is carried out in isokinetic conditions.

Yet a further purpose of the invention is to provide an apparatus that significantly reduces the overall pressure losses with respect to systems of the prior art, which would condition the isokinetic sampling and the measurement of the flow rate.

Such purposes are accomplished by the apparatus according to the present invention, and by the method that uses such an apparatus, the essential characteristics of which are defined in the independent claims attached hereto.

Further important characteristics are contained in the dependent claims.

BRIEF DESCRIPTION OF THE FIGURES

The characteristics and advantages of the apparatus of the invention and of the relative method of isokinetic sampling of the different phases in a multiphase flow will become clearer from the following description of an embodiment thereof given as an example and not for limiting purposes with reference to the attached drawings, in which.

DETAILED DESCRIPTION OF THE INVENTION

In the present invention, as described hereinafter in detail, it is presumed to conduct a continuous and simultaneous measurement of flow rate of a sampled multiphase fluid and of the same non-sampled multiphase fluid.

Figure 1:
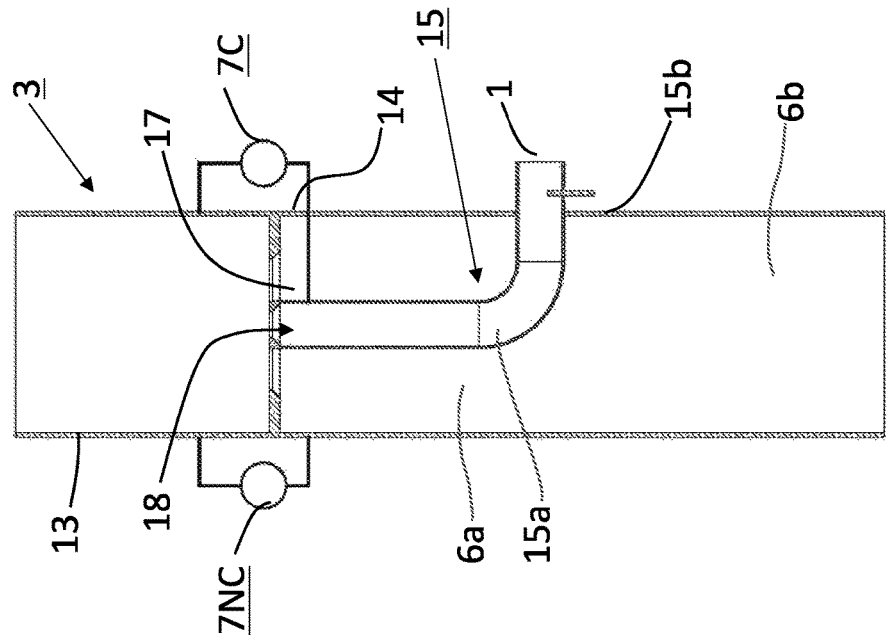
FIG. 1 compares the schematic representation of a device for: (a) isokinetic sampling for monophase stream according to the prior art; (b) isokinetic sampling for multiphase stream according to the prior art; (c) Dual Orifice Sampling according to the invention.
Figure 1:
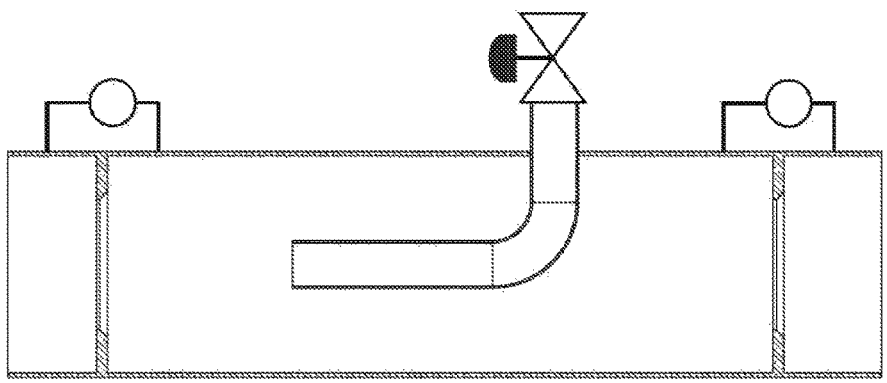
Figure 1:
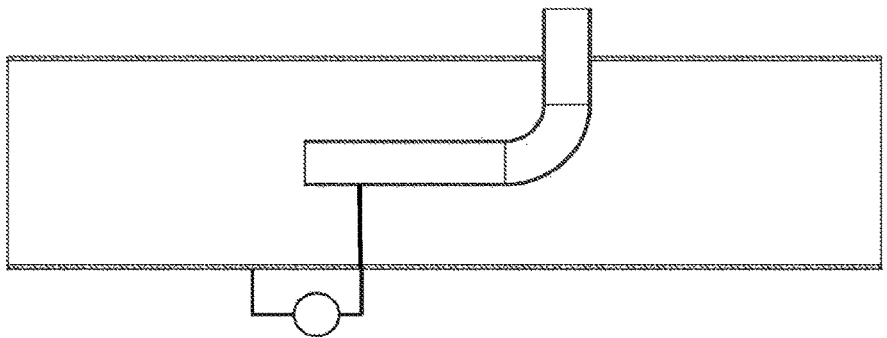
Figure 2:
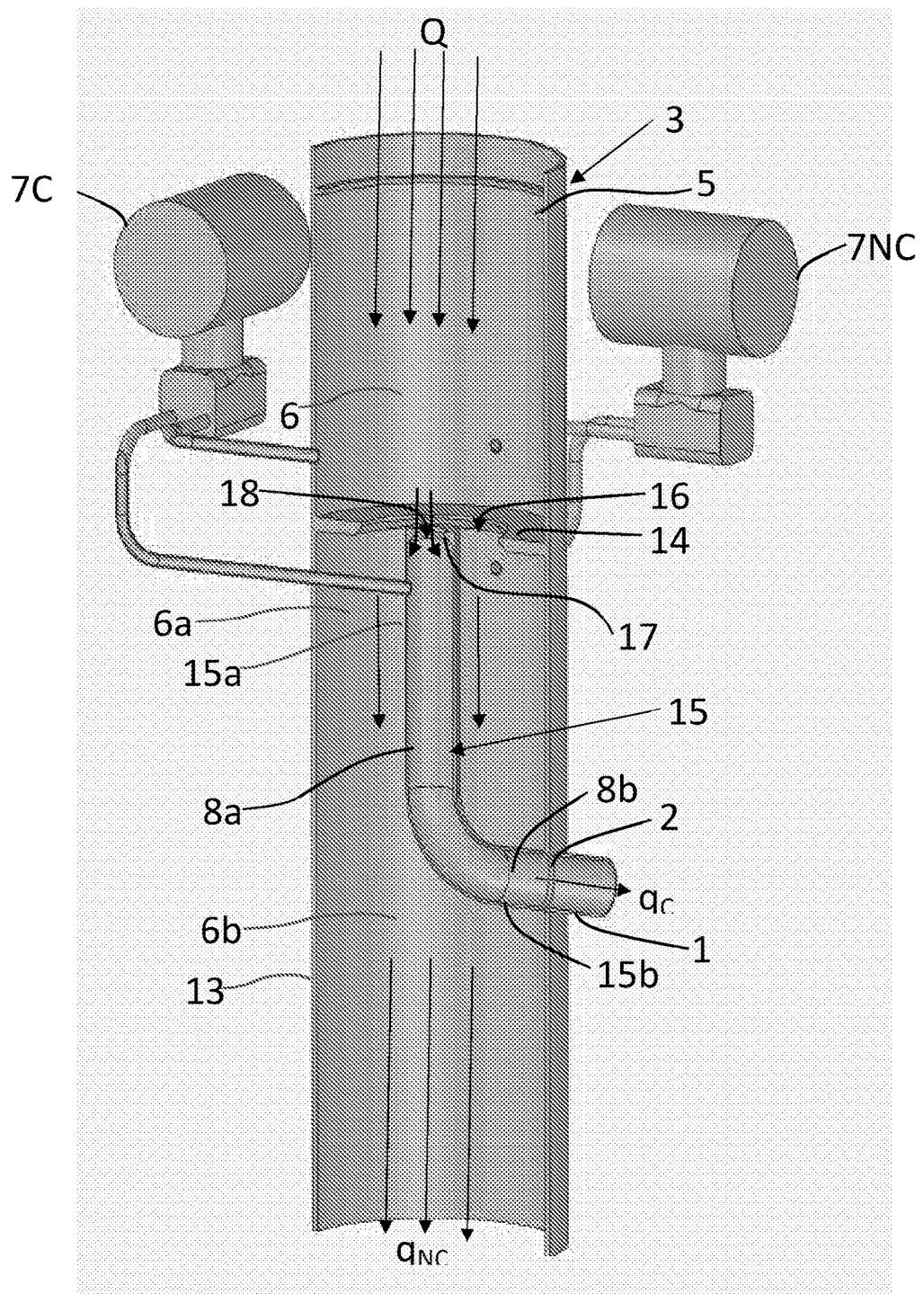
FIG. 2 represents a perspective view, partially sectioned, of a first preferred embodiment of the Dual Orifice apparatus with annular section according to the invention.

With reference to the figures, and in particular to FIG. 1c and to FIG. 2, an apparatus of the invention in a preferred embodiment thereof comprises an isokinetic sampling device 3 consisting of a tubular body 13, having a flow-through section A, inside which the multiphase stream of total flow rate Q flows.

On the inner wall of said tubular body 13 it is possible to form a rim 5 able to disrupt the possible film formed by the liquid that flows along the walls of the tubular body. Downstream of said rim 5, if present, a sampling probe 15 is positioned, essentially shaped like an L, consisting of a tubular axial portion 15a, extending inside the tubular body 13 for a part thereof, coaxially with respect to said body 13, and a tubular radial portion 15b.

Said axial portion 15a is oriented with its free end open in the direction opposite to the flow of the multiphase stream of total flow rate Q, at which an annular narrowing 17 is positioned, rigidly connected to the axial portion 15a of the probe 15 and such as to internally define a circular narrowed section, i.e. an orifice, of area $A_C$, which constitutes a sampling opening 18 of the flow rate of sampled fluid $q_C$, the underlying part of the axial portion 15a internally delimiting a vertical part 8a of the sampling channel of the probe.

The radial portion 15b of the sampling probe 15 extends from the axial region of the tubular body 3, communicating with an outlet duct 1 that extends radially and externally through an opening 2 obtained on the tubular body 13, internally delimiting a horizontal part 8b of the sampling channel.

At the same height as the sampling opening 18, inside the tubular body 13 and rigidly connected thereto, a second annular narrowing 14 is positioned having an outer diameter equal to the inner diameter of the tubular body 13 and an inner diameter greater than the outer diameter of the sampling probe 15 and such as to define, with the upper end of the sampling probe 15, an annular opening 16, i.e. an annular orifice, which constitutes the flow-through section of area $A_{NC}$ of the flow rate of non-sampled fluid $q_{NC}$. An underlying non sampling channel with annular section 6a is limited laterally by the inner cylindrical wall of the tubular body 13 and by the outer cylindrical wall of the sampling probe 15. Beneath the sampling probe 15, the part of non-sampling channel 6a with annular section takes up a circular section in a part of non-sampling channel 6b coinciding with the inside of the cylindrical body 13.

Again with reference to FIG. 2, two differential pressure measurers 7C and 7NC are in fluid communication with the inside of the tubular body 13, at suitably selected parts, so as to simultaneously measure the pressure drops of the fluid of the multiphase stream, sampled and non-sampled respectively, caused by the respective flow restrictions, according to the method described in greater detail hereinafter.

Figure 3:
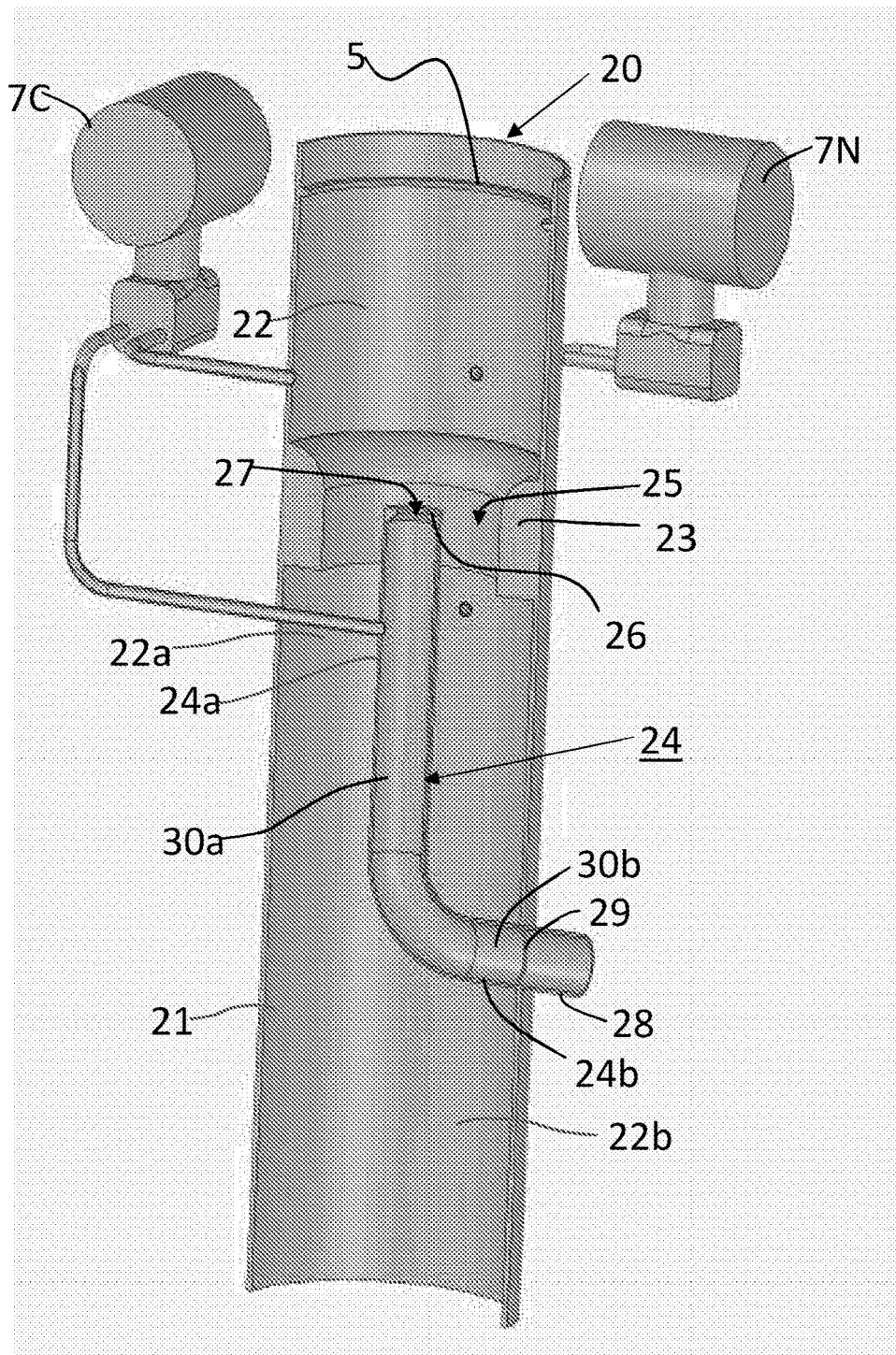
FIG. 3 shows a perspective view, partially sectioned, of a second embodiment of the Dual Orifice apparatus with annular section according to the invention.

FIG. 3 illustrates a second embodiment of the apparatus according to the present invention that, in the same way as the first embodiment of FIG. 1, also foresees flow restrictions with annular section, but the non-sampling opening with annular section is in this second embodiment defined between a nozzle-type fluid path restriction system 23, and the upper open free end of the sampling probe 24, inside which a second annular narrowing 26 is positioned, rigidly connected thereto and such as to internally define the circular sampling opening 27, arranged at the same height as the nozzle-type flow restriction 23.

In the same way as the first embodiment of FIG. 2, the second embodiment of FIG. 3 also foresees a sampling probe formed from an axial portion 24a and a radial portion 24b, the latter communicating with an outlet duct 28 that extends radially and externally through an opening 29 obtained on the tubular body 21. Inside the two portions of the probe, 24a and 24b, the horizontal part and the vertical part of the sampling channel are delimited, respectively indicated as 30a and 30b.

Beneath the non-sampling opening a non-sampling channel 22a is formed having an annular section that, beneath the sampling probe 24, coincides with the inside of the tubular body 21 in a channel having a circular section 22b.

The embodiments of the apparatus of the invention illustrated above are therefore characterised by the presence of flow restrictions inside the tubular body of the apparatus, which define narrow sections, i.e. orifices, for the multiphase fluid to flow through, one for the sampled fluid (18, 27) to flow through and at least one for the non-sampled fluid (16, 25) to pass through, which can differ in shape, but in any case are arranged parallel to one another. Such flow restrictions make it possible to carry out an effective mixing of the multiphase stream of total flow rate Q at the sampling point, and also allow the simultaneous measurement of the pressure drops of the sampled fluid and of the non-sampled fluid through suitable differential pressure measurers (7C, 7NC). In all of the configurations proposed, a non-sampling differential pressure measurer (7NC) is able to measure the pressure difference between the total fluid entering the sampling section (6, 22) and the non-sampled fluid flowing in the non-sampling section (6a, 22a) respectively upstream and downstream of the dual orifice. Similarly, a sampling differential pressure measurer (7C) is able to measure the pressure difference between the total fluid entering the sampling section (6, 22) and the sampled fluid flowing in the sampling section (8a, 30a), respectively upstream and downstream of the dual orifice.

According to a preferred embodiment of the present apparatus, a rim 5 is formed on the inner wall of the tubular body (13, 21) of the apparatus upstream of the aforementioned flow restrictions so as to create a discontinuity element on the inner wall of the tubular body and disrupt the possible film formed in the multiphase stream flowing along the walls, in this way promoting greater uniformity in the composition of the multiphase stream itself.

The rim 5 can for example consist of a ring of low thickness with respect to the diameter of the tubular body (for example of thickness corresponding to about 5% of the diameter of the tubular body) having a triangular or trapezoidal section.

The method for measuring the liquid and gaseous flow-rates $q_L$ and $q_G$ of single liquid and gaseous phases present in a stream of multiphase fluid of total flow rate Q flowing inside a tubular body according to the present invention comprises the following steps:

(i) sampling a portion of fluid $q_C$ entering through a sampling opening of section $A_C$ in which substantially isokinetic conditions occur through an isokinetic sampling device like the one of the present apparatus described above;

(ii) separation of said portion of sampled fluid $q_C$ in the single liquid and gaseous phases of flow rate respectively $q_L$ and $q_G$;

(iii) measurement of said flow-rates $q_L$ and $q_G$ of the separated liquid and gaseous phases of said sampled portion of fluid.

In the present isokinetic device a portion of fluid of flow rate $q_C$ that enters through the sampling opening (18, 27) with narrowed section of area $A_C$ flows through the duct of the sampling probe (8a,8b, 30a,30b) and is sampled. The remaining portion of fluid of flow rate $q_{NC}$, on the other hand, enters through the non-sampling opening (16, 25) with narrowed section of area $A_{NC}$ and flows inside the non-sampling duct (6a, 6b, 22a, 22b).

An innovative aspect of the apparatus and method of the present invention is represented by the way in which isokinetic sampling conditions are ensured. In the two flow restrictions the sampled flow rate $q_C$, flowing through a flow restriction, causes a load loss $\Delta p_C$ that in the case of turbulent motion of the phases can be expressed as $$\Delta p_C = \alpha_C \cdot q_C^2 / A_C^2 \qquad (3)$$

where $\alpha_C$ is the calibration coefficient of the flow restriction, a coefficient that, at least theoretically, at high flow speeds, depends exclusively on the geometry of the system and does not depend on the flow rate of the phases, i.e. for the case of flow of a single phase, on the Reynolds number of the flow.

An analogous relationship applies to the flow rate of non-sampled fluid:

$$\Delta p_{NC} = \alpha_{NC} \cdot q_{NC}^2 / A_{NC}^2, \qquad (4)$$

where $\alpha_{NC}$ is the calibration coefficient of the flow restriction flowed through by the non-sampled fraction of the overall flow.

The geometry of the present apparatus, characterised by the presence of two flow restrictions parallel to each other, is such that the ratio $\alpha_C/\alpha_{NC}$ does not change even for significant variations of the physical properties and of the flow-rates of the phases, i.e. $\alpha_C = \varphi \alpha_{NC}$, where the coefficient $\varphi$ is constant.

This corresponds to the following condition:

$$\Delta p_C = \phi \Delta p_{NC},$$

which ensures that the speed of the phases in the two orifices is the same. If the aforementioned condition (5) occurs, the preceding equations give:

$$q_c/A_c = q_{nc}/dA_{nc}, \qquad (6)$$

Indeed, since $q_c + q_{nc} = Q$ and $A_c + A_{nc} = A$, also $$q_c/A_c = Q/A, \qquad (7)$$

as required for an isokinetic sampling. The verification of the actual isokinetic nature of the sampling is carried out by checking that the relationship (7) is satisfied.

For the purposes of optimal operation of the method of the invention, it is possible to define geometries of the present apparatus such as to make the aforementioned coefficient $\phi$ substantially equal to 1. Indeed, in the at least two flow restrictions the flow rate of the respective fluid that flows through them is linked to the load loss determined by the passage through the restriction and to the section of the restriction itself by the following general relationship:

$$q = cA_0 \sqrt{\frac{2\Delta P/\rho}{1-(A_0/A)^2}} \qquad (8)$$

in which q is the flow rate of a generic fluid flowing through a restriction of section $A_0$ created in a tube of total section A, $\Delta p$ is the load loss of the fluid determined by its flowing in the restriction and p is the density of the fluid, whereas the coefficient c in the aforementioned relationship (8) gives a measurement of the load loss in the system that is caused by the narrowing of section. In a commonly used apparatus for the measurement of the flow rate of a mono-phase fluid (orifice, nozzle, Venturi tube), the coefficient c depends on the geometry of the system and on the value of the Reynolds number. For high values of the Reynolds number, the coefficient c depends exclusively on the geometry of the system and in practice is constant as the speed and the viscosity of the fluid change. When the parameter $\phi$ is equal to 1, the two coefficients c for the portions of sampled and non-sampled fluid are equal to each other, the load losses through the two flow restrictions are totally analogous. For values of $\phi$ close to 1, for example comprised between 0.9 and 1.1, the fluid-dynamic behaviour of the sampled and non-sampled fluids that flows through the at least two restrictions therefore remains totally analogous also in terms of load losses.

Experimentally, it has been found that, in the case of monophase flows, by suitably selecting the geometric parameters of the at least two flow restrictions, for example like in the embodiments of the present apparatus illustrated in FIGS. 2-3, the values of the coefficient $\varphi$ remain not only constant as the Reynolds number of the flow varies, but also comprised in a narrow range of values comprised between 0.9 and 1.1 also being able to take on values substantially equal to 1.

The separation of the liquid and gaseous phases in step ii) of the present method can be carried out using any conventional liquid-gas separator, positioned in fluid communication with the sampling device. Such a separator, having to treat only a small part of the overall flow rate, approximately comprised between 5% and 15% thereof, can be of simple structure and of very low volume.

The sampling flow-rates after the measurement in step iii), which can be carried out with monophase stream measurers also of the conventional type, possibly joined back together, are re-inserted in the main stream.

According to a preferred embodiment of the present method, the multiphase fluid is made to flow through the tubular body provided with a rim 5 upstream of the sampling, which disrupts the possible film of liquids formed along the wall of the tubular body itself, thus promoting the mixing of the total multiphase stream before sampling.

An important advantage of the present apparatus with respect to those mentioned above of the prior art is represented by the fact that the particular internal structure of the isokinetic sampling device is not a complex or bulky structure, provided with relative constructive simplicity and of low cost with respect to known devices.

A further important advantage of the apparatus of the invention is represented by the fact that both the mixing between the phases present in the multiphase stream and the measurement of the pressure drop are carried out exclusively at the two flow restrictions arranged parallel to each other, where the sampling of a portion of flow rate $q_C$ of the total flow of flow rate Q is also carried out. Therefore, in the apparatus of the invention the pressure drops caused by the mixing section of the phases that is necessary in the devices of the prior art before the sampling section do not occur, and nor do the pressure drops caused by the calibrated flange that is located downstream of the sampling section in known devices, where it is used for the continuous control of the process. The overall pressure losses in the apparatus according to the present invention are therefore significantly reduced if compared with those that can be detected in apparatuses of the prior art.

The present invention has been described up to here with reference to a preferred embodiment thereof. It should be understood that there can be other embodiments that derive from the same inventive core, all of which are covered by the scope of protection of the claims given hereafter.

The invention claimed is:

1. An apparatus for isokinetic sampling of the liquid and gaseous phases in a fluid multiphase stream, comprising:
    a sampling device for separation of said stream in a sampled fraction having a flow-rate $q_C$ and a non-sampled fraction having a flow-rate $q_{NC}$ and for sampling under substantially isokinetic conditions of a portion of fluid of said sampled fraction, said device comprising a tubular body inside of which said multiphase stream flows, and a sampling probe or sampling channel having an upper end open to the flow of said multiphase stream, and extending outside of said tubular body through an opening,
    two differential pressure gauges in fluid communication with the interior of said tubular body for simultaneously measuring pressure drops $\Delta p_C$ and $\Delta p_{NC}$ of said sampled and non-sampled fractions, caused by flow restrictions;
    a liquid-gas separator for separating the liquid and gaseous phases of said portion of sampled fraction; and
    a flow meter for measuring the flow-rates of the liquid and gaseous phases exiting from said separation means;
wherein said device for the isokinetic sampling is provided with two flow restrictions located at the same flow cross section, both normal to the flow direction, at said open end of said sampling probe or sampling channel, said restrictions having substantially annular form, being such as to cause said pressure drops and to define two narrowed, concentric flow sections of circular perimeter that constitute respectively a sampling opening having a narrowed section of area $A_C$ for the flowing of said sampled fraction and a non-sampling opening having a narrowed section of area $A_{NC}$ for the flowing of said non-sampled fraction, said sections being such that $$\Delta p_C = \alpha_C \cdot q_C^2 A_C^2 \text{ and } \Delta p_{NC} = \alpha_{NC} \cdot q_{NC}^2 / A_{NC}^2$$

wherein $\alpha_C$ and $\alpha_{NC}$ are a calibration coefficient of the section restriction through which the sampled fraction and, respectively, the non-sampled fraction flow, and are such that $\Delta p_C = \phi \Delta p_{NC}$ and $\alpha_C = \phi \alpha_{NC}$, wherein the coefficient $\phi$ is constant.

2. The apparatus according to claim 1, wherein said device for isokinetic sampling is provided with two flow restrictions in parallel between each other, defining such respective narrowed flow sections so that the coefficient $\phi$ is between 0.9 and 1.1.

3. The apparatus according to claim 2, wherein said device for isokinetic sampling is provided with two flow restrictions in parallel between each other, defining respective narrowed flow sections so that the coefficient $\phi$ is substantially equal to 1.

4. The apparatus according to claim 1, wherein said sampling probe consists of a tubular axial portion extending inside said tubular body for a part and coaxially to and of a tubular radial portion, and said device is provided with two annular flow restrictions, a first restriction rigidly connected to said axial portion of the sampling probe and defining a circular, narrowed section for the flowing through of said sampled fraction through a sampling opening, and a second restriction rigidly connected to said tubular body and defining, together with said upper end of said probe, an annular narrowed section for the flowing through of said non-sampled fraction through a non-sampling opening.

5. The apparatus according to claim 4, wherein said second restriction consists of a nozzle-type fluid path restriction element.

6. The apparatus according to claim 1, further comprising a rim formed on the inner wall of the tubular body of the apparatus upstream of said restrictions.

7. A method for isokinetic sampling of the liquid and gaseous phases in a fluid multiphase stream flowing inside a tubular body, comprising sampling of a portion of said fluid stream entering through a sampling opening wherein there exist substantially isokinetic conditions, by means of a device for isokinetic sampling as defined in claim 1.

8. The method according to claim 7, further comprising, before said sampling, the flowing of said multiphase fluid through a portion of said tubular body provided with a rim able to disrupt a possible film of liquids that forms along the wall of the tubular body itself.

9. A method for the measurement of the liquid and gaseous flow-rates $q_L$ and $q_G$ of the liquid and gaseous phases in a fluid multiphase stream of a total flow-rate Q flowing inside a tubular body comprising isokinetic sampling of a portion of said multiphase stream having a flow-rate $q_C$ according to the method defined in claim 7, followed by separation of said portion of flow-rate $q_C$ in the single liquid and gaseous phases of flow-rates $q_L$ and $q_G$, which are then measured.

10. The method according claim 9, further comprising a step wherein said flow-rates $q_L$ and $q_G$ of the liquid and gaseous phases, once measured and possibly combined, are re-introduced in said multiphase stream inside said tubular body.

* * * * *